(12) United States Patent
Melkent et al.

(10) Patent No.: US 7,815,683 B2
(45) Date of Patent: Oct. 19, 2010

(54) IMPLANTS WITH HELICAL SUPPORTS AND METHODS OF USE FOR SPACING VERTEBRAL MEMBERS

(75) Inventors: Anthony J. Melkent, Memphis, TN (US); Jonathan M. Dewey, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1021 days.

(21) Appl. No.: 11/549,791

(22) Filed: Oct. 16, 2006

(65) Prior Publication Data

US 2008/0161926 A1 Jul. 3, 2008

(51) Int. Cl.
*A61F 2/44* (2006.01)

(52) U.S. Cl. .................. 623/17.16; 248/418; 623/17.11

(58) Field of Classification Search ... 623/17.11–17.16; 606/300–322, 326–328, 63, 68, 90; 254/93 H, 254/98, 100, 102; 248/418
See application file for complete search history.

(56) References Cited

U.S. PATENT DOCUMENTS

| 4,554,914 | A | 11/1985 | Kapp et al. |
|---|---|---|---|
| 4,657,550 | A | 4/1987 | Daher |
| 4,820,305 | A | 4/1989 | Harms et al. |
| 4,932,975 | A | 6/1990 | Main et al. |
| 5,062,850 | A | 11/1991 | MacMillan et al. |
| 5,236,460 | A | 8/1993 | Barber |
| 5,336,223 | A | 8/1994 | Rogers |
| 5,360,430 | A | 11/1994 | Lin |
| 5,480,442 | A | 1/1996 | Bertagnoli |
| 5,571,190 | A | 11/1996 | Ulrich et al. |
| 5,571,192 | A | 11/1996 | Schonhoffer |
| 5,702,451 | A | 12/1997 | Biedermann et al. |
| 5,702,453 | A | 12/1997 | Rabbe et al. |
| 5,702,455 | A | 12/1997 | Saggar |
| 5,723,013 | A | 3/1998 | Jeanson et al. |
| 5,725,528 | A | 3/1998 | Errico et al. |
| 5,776,197 | A | 7/1998 | Rabbe et al. |
| 5,776,198 | A | 7/1998 | Rabbe et al. |
| 5,972,031 | A * | 10/1999 | Biedermann et al. ..... 623/17.16 |
| 5,989,290 | A | 11/1999 | Biedermann et al. |
| 6,015,436 | A | 1/2000 | Schonhoffer |
| 6,086,613 | A | 7/2000 | Camino et al. |
| 6,156,038 | A | 12/2000 | Zucherman et al. |

(Continued)

FOREIGN PATENT DOCUMENTS

EP 1 080 703 A2 3/2001

(Continued)

*Primary Examiner*—Eduardo C Robert
*Assistant Examiner*—Summer L Kostelnik (57) ABSTRACT

The present application is directed to implants with inner and outer members positioned in a telescoping arrangement. The members may include helical supports to selectively adjust the height of the implant. The helical supports offer a large contact surface to prevent inadvertent reduction of the length due to application of a compressive force. In some embodiments, the helical support members may be shaped to facilitate movement of the members to increase the height. The shape may further prevent movement that would decrease the height. Some embodiments may also prevent relative rotation of the members. In use, the inner and outer members are moved apart to adjust the height of the implant to space apart the vertebral members. The members may further be constructed to prevent the members from moving together after insertion between the vertebral members.

20 Claims, 9 Drawing Sheets

U.S. PATENT DOCUMENTS

| | | | |
|---|---|---|---|
| 6,176,881 | B1 | 1/2001 | Schar et al. |
| 6,190,413 | B1 | 2/2001 | Sutcliffe |
| 6,193,755 | B1 | 2/2001 | Metz-Stavenhagen et al. |
| 6,193,756 | B1 | 2/2001 | Studer et al. |
| 6,200,348 | B1 | 3/2001 | Biedermann et al. |
| 6,296,665 | B1 | 10/2001 | Strnad et al. |
| 6,299,644 | B1 | 10/2001 | Vanderschot |
| 6,344,057 | B1 | 2/2002 | Rabbe et al. |
| 6,352,556 | B1 | 3/2002 | Kretschmer et al. |
| 6,375,681 | B1 | 4/2002 | Truscott |
| 6,375,683 | B1 | 4/2002 | Crozet et al. |
| 6,395,034 | B1 | 5/2002 | Suddaby |
| 6,409,766 | B1 | 6/2002 | Brett |
| 6,447,547 | B1 | 9/2002 | Michelson |
| 6,454,806 | B1 | 9/2002 | Cohen et al. |
| 6,520,991 | B2 | 2/2003 | Huene |
| 6,524,341 | B2 | 2/2003 | Lang et al. |
| 6,562,074 | B2 | 5/2003 | Gerbec et al. |
| 6,616,695 | B1 | 9/2003 | Crozet et al. |
| 6,645,249 | B2 | 11/2003 | Ralph et al. |
| 6,648,917 | B2 | 11/2003 | Gerbec et al. |
| 6,660,038 | B2 | 12/2003 | Boyer, II et al. |
| 6,719,796 | B2 | 4/2004 | Cohen et al. |
| 6,752,832 | B2 | 6/2004 | Neumann |
| 6,758,862 | B2 | 7/2004 | Berry et al. |
| 6,776,798 | B2 | 8/2004 | Camino et al. |
| 6,783,547 | B2 | 8/2004 | Castro |
| 6,793,678 | B2 | 9/2004 | Hawkins |
| 6,808,538 | B2 | 10/2004 | Paponneau |
| 6,866,682 | B1 | 3/2005 | An et al. |
| 6,908,485 | B2 | 6/2005 | Crozet et al. |
| 2003/0191531 | A1 | 10/2003 | Berry et al. |
| 2003/0199980 | A1 | 10/2003 | Siedler |
| 2004/0049271 | A1 | 3/2004 | Biedermann et al. |
| 2004/0073314 | A1 | 4/2004 | White et al. |
| 2004/0172129 | A1 | 9/2004 | Schafer et al. |
| 2004/0181283 | A1 | 9/2004 | Boyer et al. |
| 2004/0186569 | A1 | 9/2004 | Berry |
| 2005/0004572 | A1 | 1/2005 | Biedermann et al. |
| 2005/0060036 | A1 | 3/2005 | Schultz et al. |
| 2005/0090898 | A1 | 4/2005 | Berry et al. |
| 2005/0113921 | A1 | 5/2005 | An et al. |

FOREIGN PATENT DOCUMENTS

| | | |
|---|---|---|
| EP | 1 188 424 A1 | 3/2002 |
| WO | WO 04/096103 A1 | 4/2003 |
| WO | WO 03/096937 A1 | 5/2003 |

* cited by examiner

IMPLANTS WITH HELICAL SUPPORTS AND METHODS OF USE FOR SPACING VERTEBRAL MEMBERS

BACKGROUND

The present application is directed to devices and methods for spacing vertebral members, and more particularly, to intervertebral implants with inner and outer members each with one or more helical supports to selectively adjust the height of the implant.

The spine is divided into four regions comprising the cervical, thoracic, lumbar, and sacrococcygeal regions. The cervical region includes the top seven vertebral members identified as C1-C7. The thoracic region includes the next twelve vertebral members identified as T1-T12. The lumbar region includes five vertebral members L1-L5. The sacrococcygeal region includes nine fused vertebral members that form the sacrum and the coccyx. The vertebral members of the spine are aligned in a curved configuration that includes a cervical curve, thoracic curve, and lumbosacral curve. Intervertebral discs are positioned between the vertebral members and permit flexion, extension, lateral bending, and rotation.

Various conditions may lead to damage of the intervertebral discs and/or the vertebral members. The damage may result from a variety of causes including a specific event such as trauma, a degenerative condition, a tumor, or infection. Damage to the intervertebral discs and vertebral members can lead to pain, neurological deficit, and/or loss of motion.

Various procedures include replacing the entirety or a section of a vertebral member, the entirety or a section of an intervertebral disc, or both. One or more replacement implants may be inserted to replace the damaged vertebral members and/or discs. The implants reduce or eliminate the pain and neurological deficit, and increase the range of motion.

SUMMARY

The present application is directed to implants with inner and outer members positioned in a telescoping arrangement. The members may include helical supports to selectively adjust the height of the implant. The helical supports offer a large contact surface to prevent inadvertent reduction of the length due to application of a compressive force. In some embodiments, the helical support members may be shaped to facilitate movement of the members to increase the height. The shape may further prevent movement that would decrease the height. Some embodiments may also prevent relative rotation of the members. In use, the inner and outer members are moved in an outward direction to adjust the height of the implant and space apart the vertebral members. The members may further be constructed to prevent the members from moving together after insertion between the vertebral members.

DETAILED DESCRIPTION

The present application is directed to implants and methods of spacing apart vertebral members. The implants may be used for replacement of a vertebral member such as during a corpectomy procedure, replacement of an intervertebral disc during a discectomy procedure, or replacement of both a vertebral member and intervertebral disc. The implants are constructed of inner and outer members that include helical supports for relative movement in a first direction to selectively adjust a height of the implant. The supports engage together to prevent the relative movement of the members in a second direction after insertion within the patient that would decrease the height of the implant.

Figure 1:
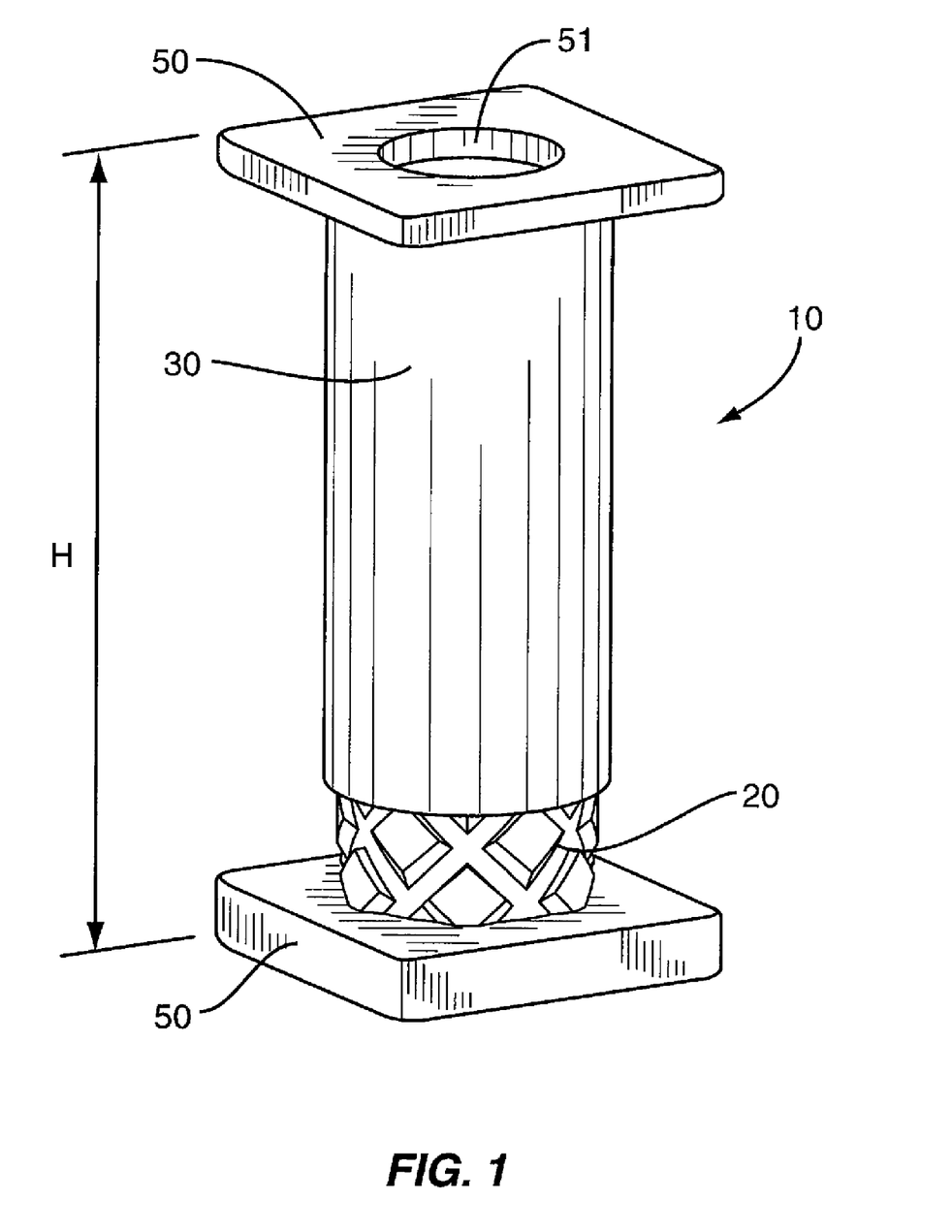
FIG. 1 is a perspective view of an implant according to one embodiment.

FIG. 1 illustrates one embodiment of an implant 10. The implant 10 includes inner and outer members 20, 30 arranged in a telescoping configuration. Helical supports are positioned on the exterior of the inner member 20 and interior of the outer member 30. The helical supports maintain the height H of the implant 10 after insertion within the patient. The supports also provide for relative movement of the members 20, 30 in an outward direction to increase the height H, and prevent or restrict relative movement of the members 20, 30 in an inward direction that would decrease the implant height.

Figure 2:
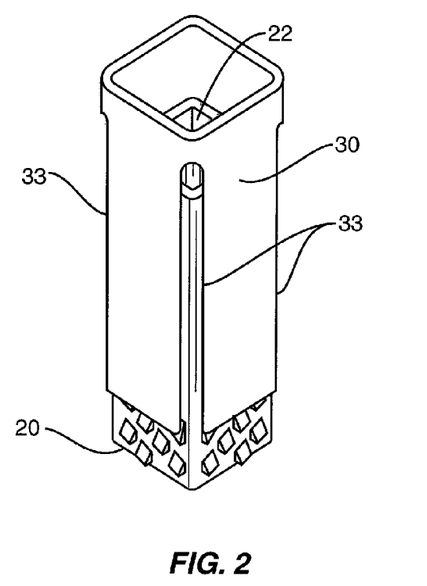
FIG. 2 is a perspective view of an implant according to one embodiment.

Members 20, 30 may include a variety of different cross-sectional shapes and sizes. The shapes and sizes of the members 20, 30 provide for relative axial movement to adjust the height H, and also for the helical supports to engage together. FIGS. 1 illustrates an embodiment with tubular members 20, 30 including a circular cross-sectional shape. FIG. 2 illustrates an embodiment with a rectangular cross-sectional shape, and FIG. 3 includes a triangular cross-sectional shape. In these embodiments, the cross-sectional shapes of the members 20, 30 are the same. In other embodiments, the shapes may be different provided they allow for axial movement and for engagement of the helical supports.

Figure 4:
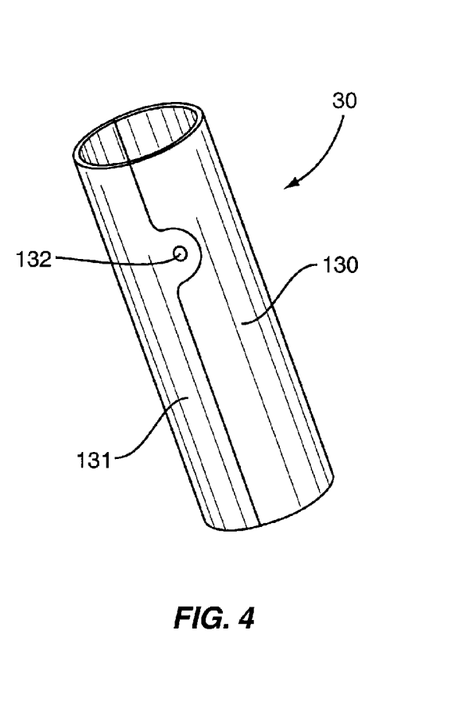
FIG. 4 is a perspective view of an outer member according to one embodiment.

One or both members 20, 30 may be constructed as a single piece such as illustrated in FIG. 1. Members 20, 30 may also be constructed from multiple pieces as illustrated in FIG. 4. In this embodiment, member 30 comprises first and second sections 130, 131 connected together with one or more fasteners 132. Each of the members 130, 131 are semi-cylindrical and connect together to form the overall cylindrical member 30. The connection may provide for the members 130, 131 to pivot about the fastener(s) 132 to provide ratcheting action during axial movement of the members 20, 30 as will be explained in detail.

Figure 5:
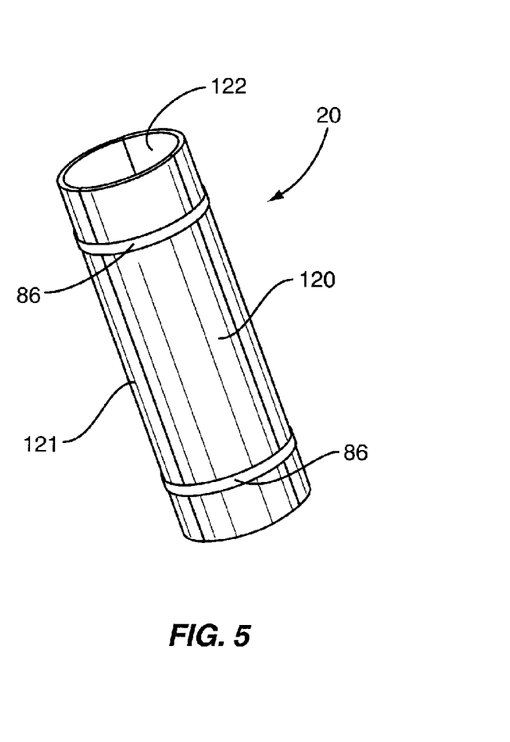
FIG. 5 is a perspective view of an outer member according to one embodiment.

One or more bands 86 may also attach multiple sections of the members 20, 30 together. FIG. 5 includes a pair of bands 86 that extend around sections 120, 121, and 122 to form member 20. Bands 86 may be constructed of flexible or inflexible materials.

Figure 3:
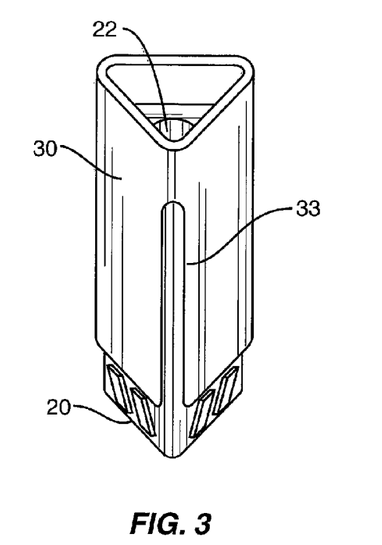
FIG. 3 is a perspective view of an implant according to one embodiment.
Figures 6, 7:
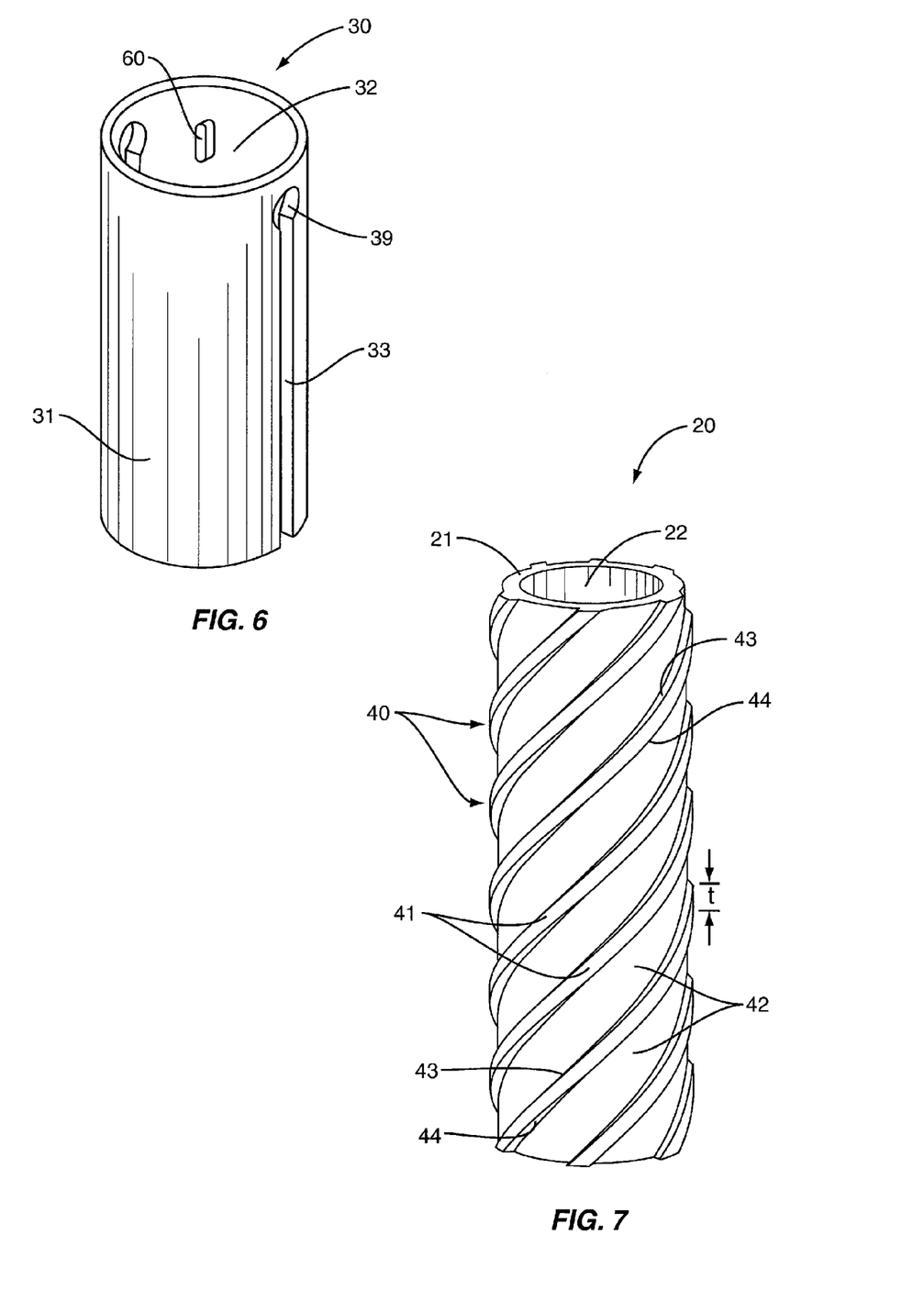
FIG. 6 is a perspective view of an outer member according to one embodiment.
FIG. 7 is a side view of an inner member according to one embodiment.

Outer member 30 includes a body 31 with a hollow interior 32. One or more slots 33 may extend along a longitudinal length of the body 31. The slots 33 allow the body 31 to move radially in a ratcheting manner during movement of the members 20, 30 as will be explained below. In the embodiment of FIG. 6, two slots 33 extend axially along a section of the length and are positioned on opposing sides of the body 31. A hinge 39 may be positioned at the end of the slots 33. Hinge 39 may include an enlarged opening integral with the slot 33 for ratcheting motion of the slotted body. In some embodiments as illustrated in FIGS. 2 and 3, slots 33 are positioned in the corners of the polygonal outer members 30.

Inner member 20 is sized to fit within the outer member 30. Inner member 20 includes a body 21 with a hollow interior 22. A centerline of the inner member 20 is substantially aligned with a centerline of the outer member 30. Inner member 20 may be the same or different height as the outer member 30.

Endplates 50 may be positioned on one or more of the members 20, 30 to contact the vertebral members as illustrated in FIG. 1. The endplates 50 may include a variety of shapes and sizes depending upon the context of use. In one embodiment, an opening 51 is positioned on one or both endplates 50. Opening 51 leads into the interiors 22, 32 of the members 20, 30. Graft material may be placed within the center of the implant 10 to facilitate bone growth and fusion with the vertebral members. In another embodiment, the members 20, 30 directly contact the vertebral members (i.e., no endplates 50). The outer surfaces of the endplates 50 or members 20, 30 may include teeth to bite into the vertebral members and maintain the position of the implant 10. Teeth may include a variety of shapes and sizes. The outer surfaces may also include a roughened surface to facilitate contact with the vertebral member.

Helical supports 40 extend from the exterior of the inner member 20 and the interior of the outer member 30. The helical supports 40 engage together to maintain the height H of the implant 10 under a compressive load. The helical supports 40 may also allow for outward axial movement of the members 20, 30 to enlarge the height as necessary. Helical supports 40 may include a variety of shapes and sizes. The helical supports on the members 20, 30 may be the same or different, may continuously extend around the members 20, 30, or may be discontinuous comprising one or more discrete sections. Further, multiple helical supports 40 may be positioned on one or both members 20, 30.

Figure 8:
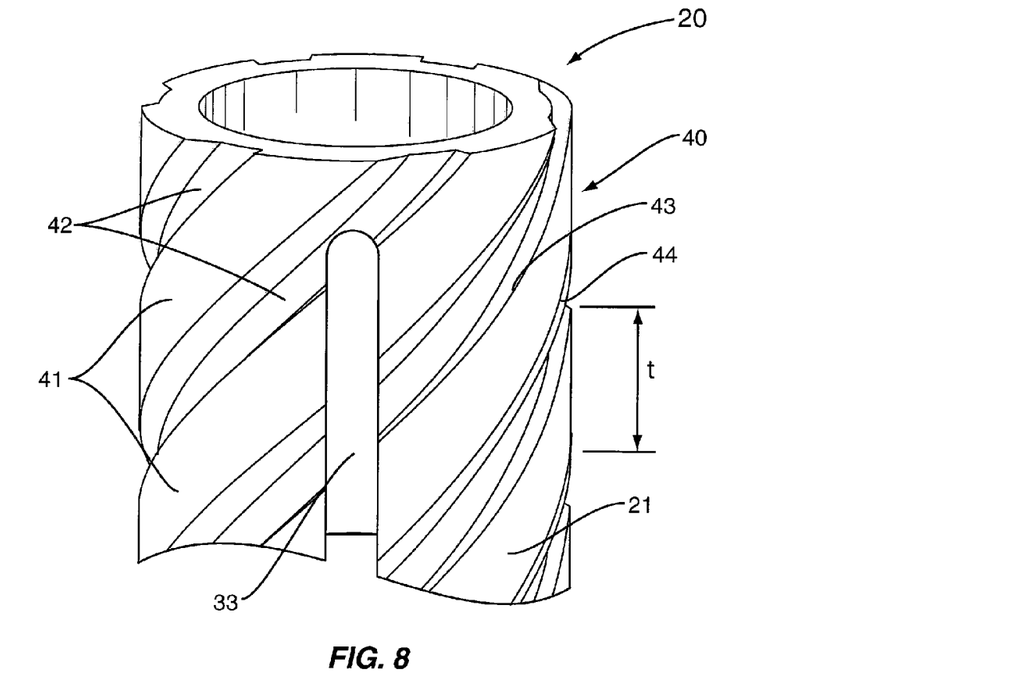
FIG. 8 is a perspective view of an inner member according to one embodiment.

FIG. 7 illustrates one embodiment of a helical support 40 extending around the inner member 20. Support 40 includes a helical spline 41. Wraps of the spline 41 are separated by a cut 42. Spline 41 includes a thickness t defined between superior and inferior sides 43, 44. The distance between wraps of the spline 41, and the angle of the spline 41 may vary depending upon the context. FIG. 8 illustrates a similar embodiment with a helical spline 41 separated by a cut 42. The thickness t of the spline 41 is greater and the cut 42 is narrower than that of FIG. 7.

Figure 9:
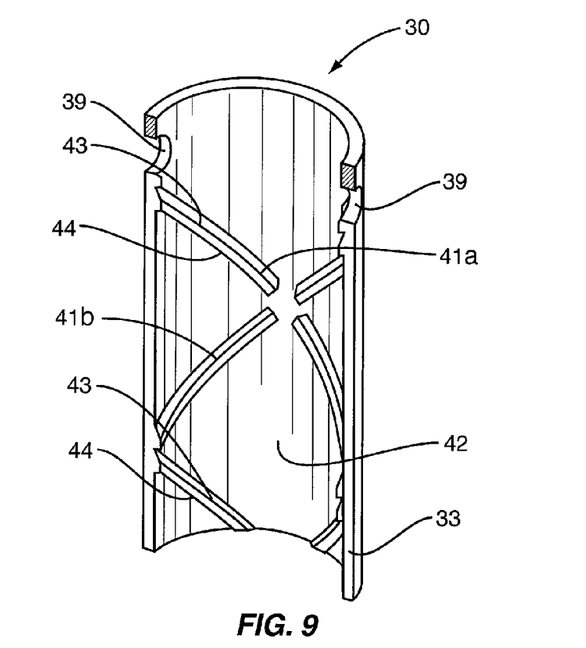
FIG. 9 is a section view of an outer member according to one embodiment.

Multiple helical supports 40 may extend around the members 20, 30. FIG. 9 includes a first helical spline 41a extending in a first direction, and second helical spline 41b in a second direction. Each spline 41a, 41b includes a superior side 43 and an inferior side 44. Cuts 42 are positioned between the splines 41a, 41b. In this embodiment, splines 41a, 41b are substantially the same shape and size. In other embodiments, the splines 41a, 41b may be different.

Figure 10A:
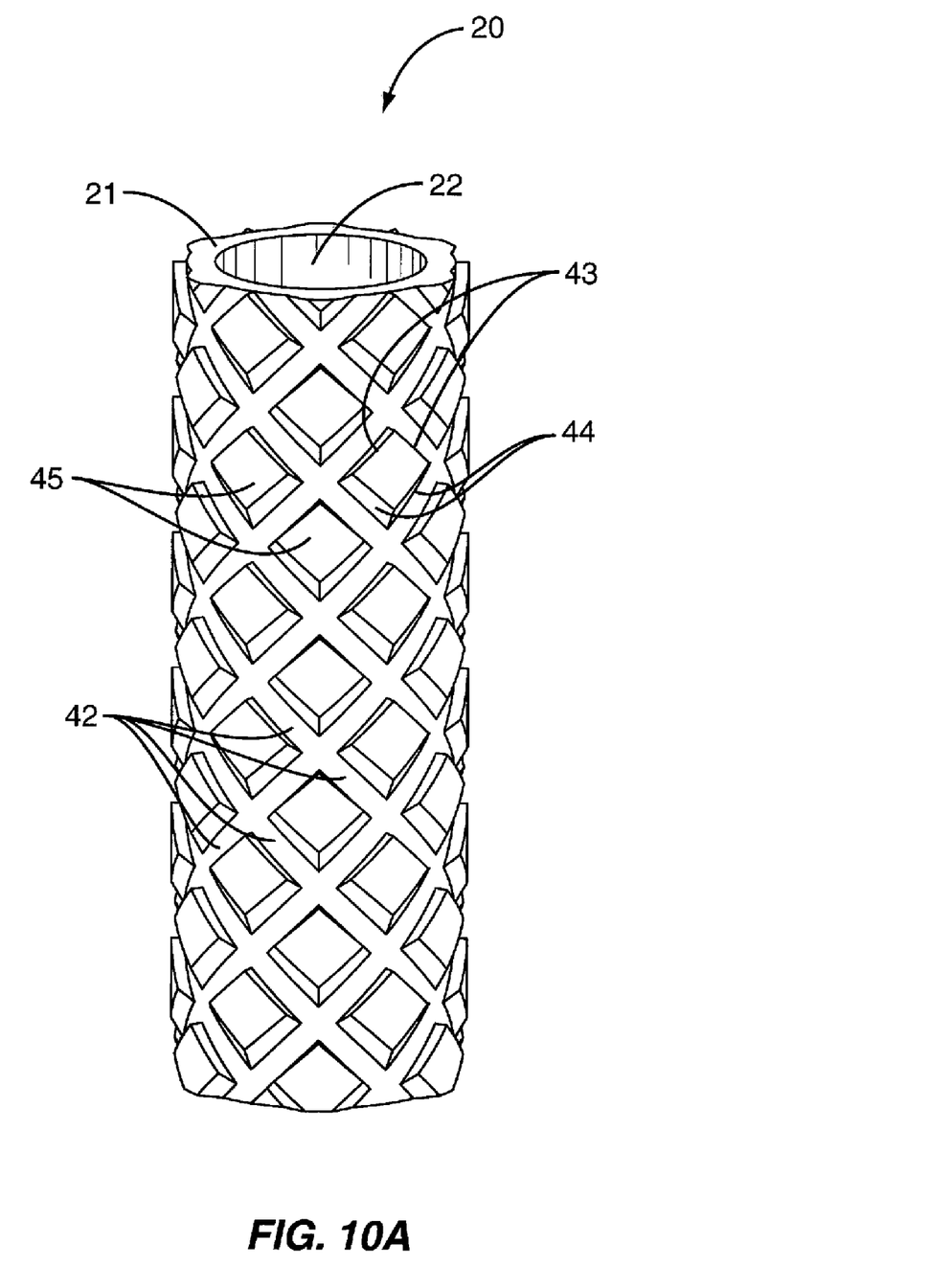
FIG. 10A is a perspective view of an inner member according to one embodiment.
Figure 10B:
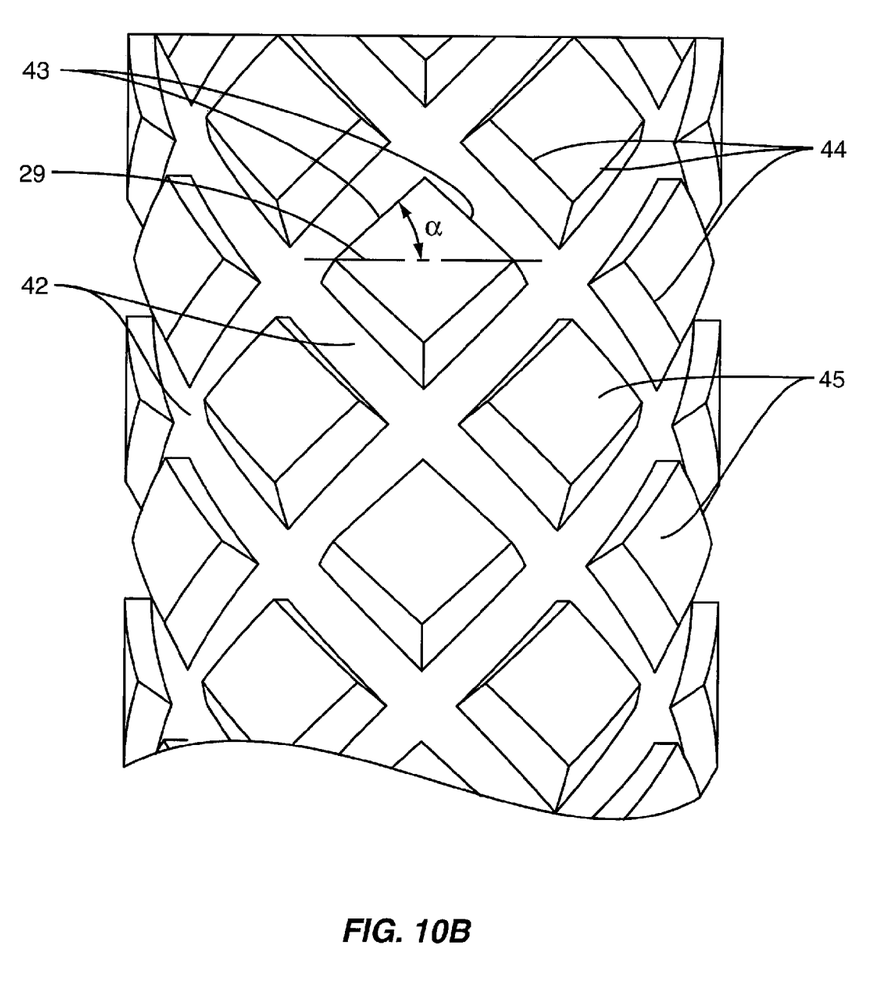
FIG. 10B is a detail view of a portion of the inner member of FIG. 10A.

Helical supports 40 may also include teeth 45 as illustrated in FIGS. 10A and 10B. Teeth 45 each include one or more superior sides 43 and inferior sides 44. Cuts 42 are positioned adjacent to each of the sides 43, 44. Teeth 45 may further include an outer surface that in this embodiment is substantially smooth. The teeth 45 and cuts 42 are spaced in helical patterns along the body 21. The teeth 45 and cuts 42 generally form a first helical spline that wraps around the body 21 in a first direction, and a second helical spline that wraps around the body in a second direction.

Figure 11:
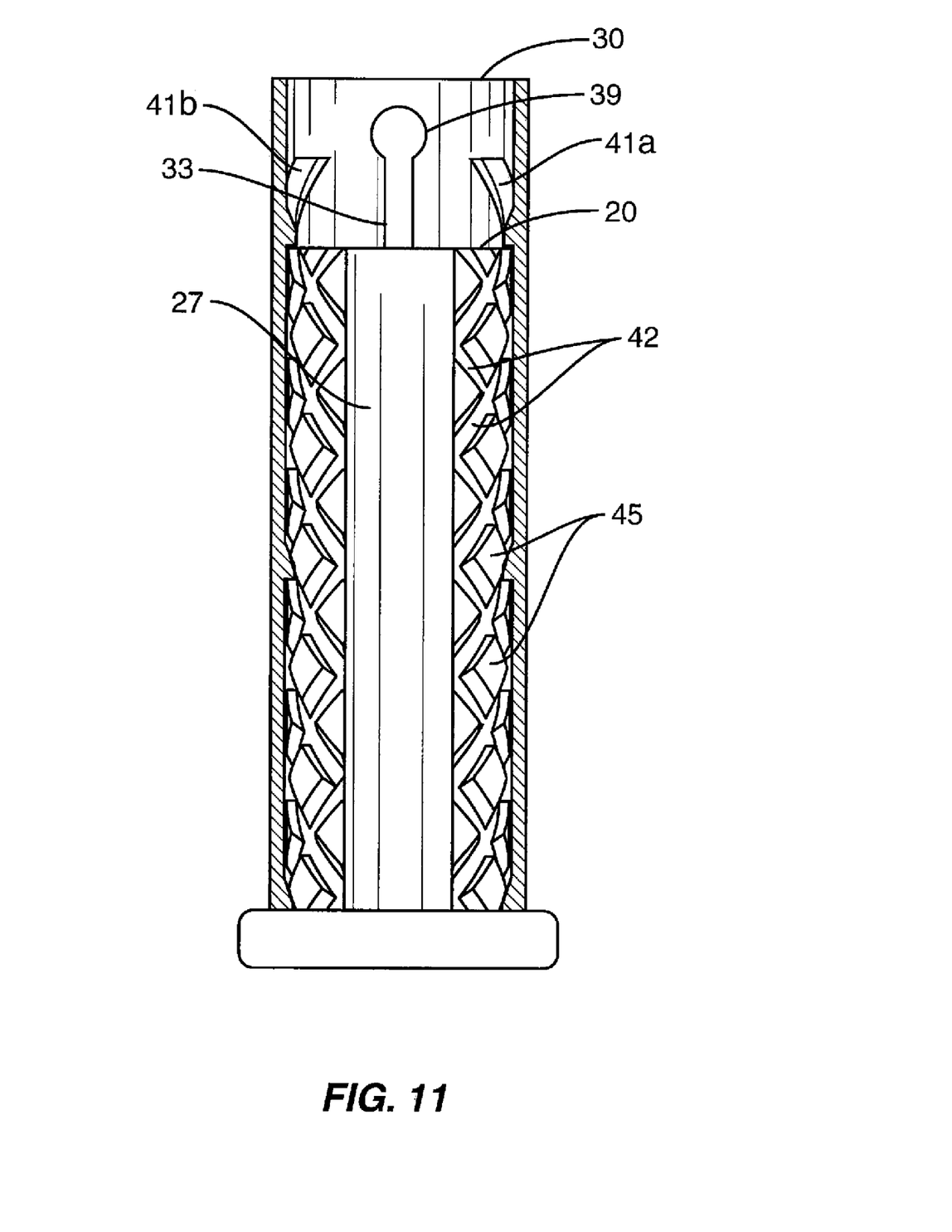
FIG. 11 is a cut-away view of an inner member within an outer member according to one embodiment.

In some embodiments, the helical supports 40 are the same on each of the members 20, 30. By way of example, each of the members 20, 30 may include a plurality of teeth 45. Alternatively, the helical supports 40 may be different. FIG. 11 illustrates an embodiment with the members 20, 30 including different helical supports 40 with the inner member 20 including teeth 45 that engage with splines 41a, 41b of the outer member 30.

Figure 12A:
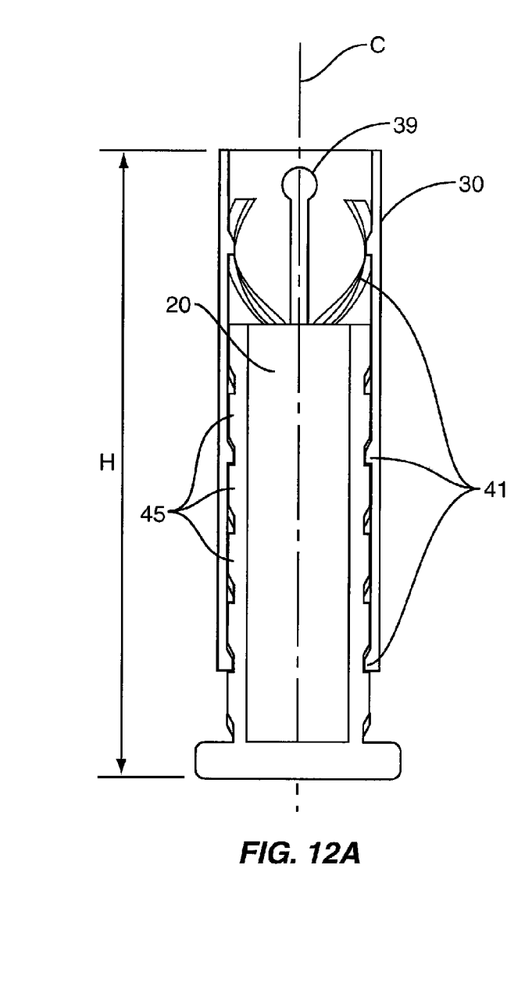
FIGS. 12A, 12B, and 12C are side schematic views illustrating relative positions of inner and outer members according to one embodiment.
Figure 12B:
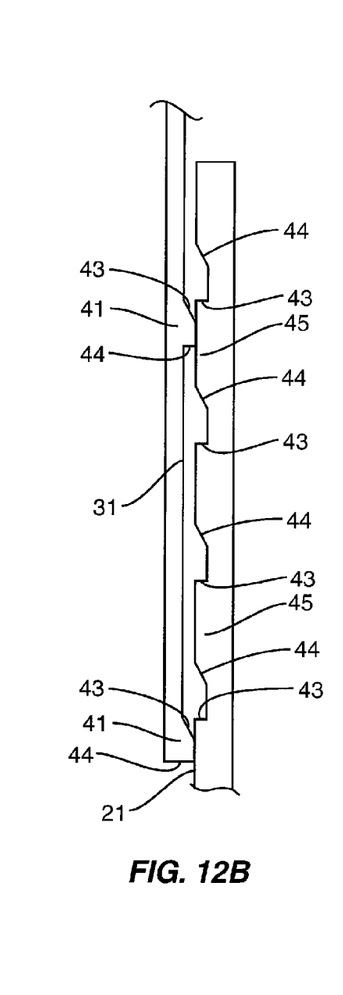
Figure 12C:
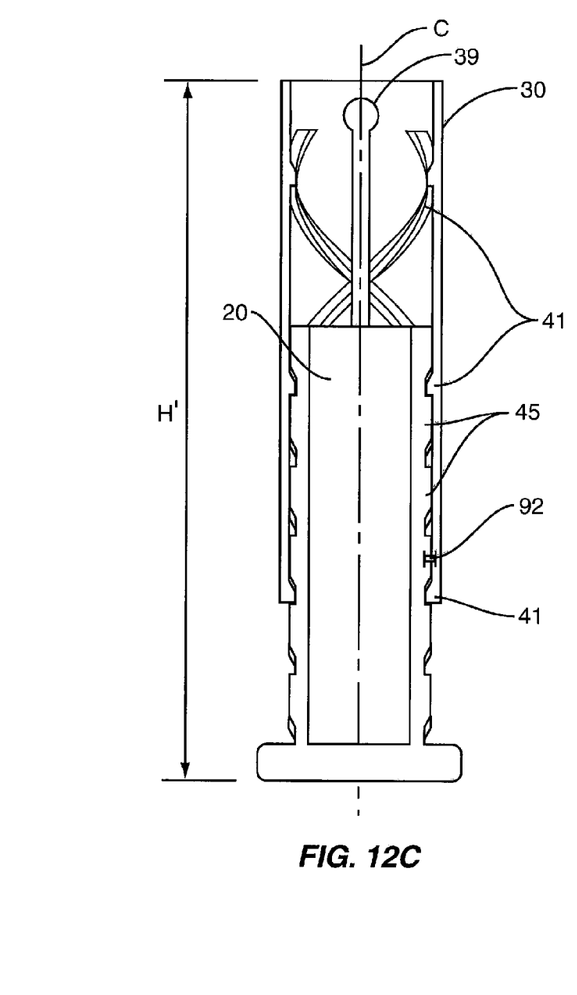

Movement of the inner member 20 relative to the outer member 30 adjusts the height H of the implant 10. FIGS. 12A-12C illustrate one embodiment of this movement that expands the height of the implant 10 from H to H'. In this embodiment, the inner member 20 includes teeth 45 and the outer member 30 includes a pair of splines 41. As illustrated in FIG. 12A, implant 10 includes a first height H. The splines 41 and teeth 45 are engaged together to maintain the first height H with the inferior sides 44 of the splines 41 in contact against the superior sides 44 of the teeth 45.

The sides 43, 44 of the helical supports 40 may be configured to facilitate outward movement, and prevent inward movement. The inferior sides 44 of the splines 41 and superior sides 43 of the teeth 45 are disposed at a steep angle that prevents inward movement when a compressive load is applied to the implant 10. In this embodiment, sides 44, 45 each extend outward from their respective bodies at substantially 90°. In another embodiment, the sides 44, 45 are undercut to engage together and prevent inward movement.

An increase in height is accomplished by applying an outward distraction force along the line C. The force causes the outer member 30 to move outward relative to the inner member 20 and helical support members 40 to slide across each other as illustrated in FIG. 12B. Specifically, the splines 41 and teeth 45 move from the opposing cuts 42 and slide across each other. This outward movement of the support members 40 is facilitated by the superior sides 43 of the splines 41 and inferior sides 44 of the teeth 45 being disposed at a shallow angle. The movement further causes the outer surface of the splines 41 to slide along the surfaces of the teeth 45. In one embodiment, each of the outer surfaces is substantially smooth to facilitate the sliding movement.

The outward movement may further be assisted by the expansion of the body 31. This expansion may be caused by the flexibility of one or both of the members 20, 30. Expansion may also be caused by a radial expansion of the outer member 30 due to the one or more longitudinal slots 33. The slots 33 provide for the outer member 30 to radially expand thus allowing the helical support member 40 on the outer member 30 to engage and disengage with the inner member 20. In large expansion movements, the outer member 30 moves in a ratcheting motion as the support member 40 moves past the opposing support member 40 on the inner member 20. Using FIG. 12B as an example, the ratcheting motion is caused as the splines 41 slide past the multiple teeth 45 and cuts 42. The movement of the support members 40 may further provide tactile feedback to the surgeon to determine the expansion of the implant 10.

FIG. 12C illustrates the outer member 30 attached at a higher location along the inner member 20 with the implant 10 now including a greater height H'. The splines 41 are again engaged within the teeth 45 to prevent inward movement.

Slots 33 may be positioned on the outer member 30 for outward radial movement as described in FIGS. 12A-12C. In another embodiment, one or more slots 33 may be positioned along the longitudinal length of the inner member 20. Slots 33 cause the inner member 20 to move radially inwardly thus allowing for the helical supports 40 to slide past one another.

The helical supports 40 may not extend along sections of the members 20, 30 that are not slotted. As illustrated in FIG. 9, the splines 41a, 41b extend from a lower edge of the body to the hinges 39. The section above the hinges 39 may not allow for radial movement. Helical supports 40 positioned in this non-slotted section may not be able to become disengaged from the corresponding helical supports 40 and therefore prevent axial expansion of the implant 10.

The implant 10 may also prevent the relative rotation of the members 20, 30. In one embodiment, rotation is prevented due to the shape of the inner members 20, 30. FIGS. 2 and 3 illustrate embodiments with the shapes of the members 20, 30 preventing rotation.

One embodiment includes one or more extensions 60 that extend between the members 20, 30. Extensions 60 fit within a slot 33 to prevent rotation and allow for axial movement. FIG. 6 illustrates one embodiment with the extension 60 extending inward into the interior 32 of the outer member 30. The extension 60 is sized to fit within a longitudinal slot 33 in the inner member 20 such as a slot 33 illustrated in FIG. 8. The extension 60 may include a variety of shapes and sizes to fit within the slot 33. Extensions 60 may extend from either of the members 20, 30 to fit within opposing slots 33. Further, multiple extensions 60 may be positioned along the members 20, 30 to fit within one or more slots 33.

Figure 14:
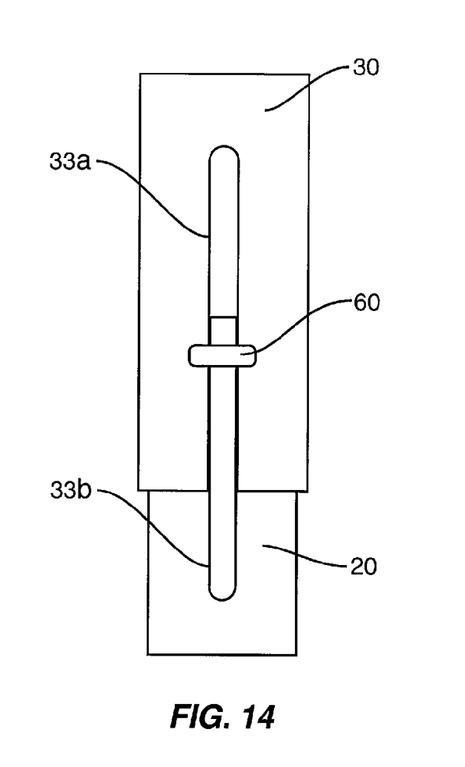
FIG. 14 is a side view of an extension positioned within mating slots according to one embodiment.
Figure 15:
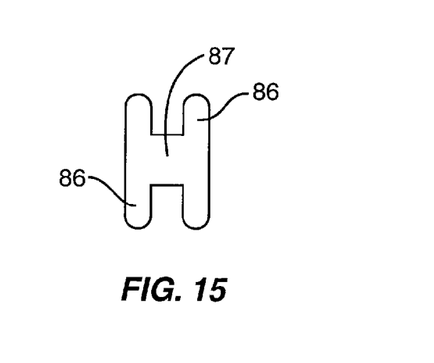
FIG. 15 is a side view of an extension according to one embodiment.

In another embodiment as illustrated in FIG. 14, extension 60 is a separate member that fits within slots 33a, 33b. The extension 60 may move axially within the combined slots 33a, 33b. Extension 60 allows for axial movement of the members 20, 30, yet prevents rotation. FIG. 15 illustrates an embodiment of the extension 60 that includes a core 87 and opposing wings 86. Core 87 is sized to move along the slots 33a, 33b, while the wings 86 prevent escape.

The members 20, 30 may include a stop mechanism to control the extent of axial movement in the outward direction. In one embodiment, each member 20, 30 includes a rim that contact together and prevent further axial movement.

Rotation prevention may also be caused by multiple helical supports 40 that wrap in different directions around one of the members 20, 30. The opposing helical supports 40 bind together to prevent relative rotation.

The angle of incidence α is formed between a superior side 43 and a horizontal line that extends through the helical support 40 as illustrated in FIG. 10B. The angle of incidence α of the helical supports 40 may vary depending upon the context. In one embodiment, the angle α is about 45°.

One or more fasteners 92 may be inserted within the members 20, 30 to lock the implant height as illustrated in FIG. 12C. Fasteners 92 are inserted through the outer member 30 to contact the inner member 20. The fasteners 92 may contact the outer surface of the inner member 20, or extend into an aperture in the body 21. Fasteners 92 may include a variety of configurations including but not limited to screws, rivets, pins, and clips.

In one embodiment as illustrated in FIG. 10A, helical supports 40 are positioned about the entirety of the members 20, 30. In other embodiments, the inner member 20 may include areas on the members 20, 30 that do not include helical supports 40. The size of these areas may vary depending upon the context of use.

Figure 13:
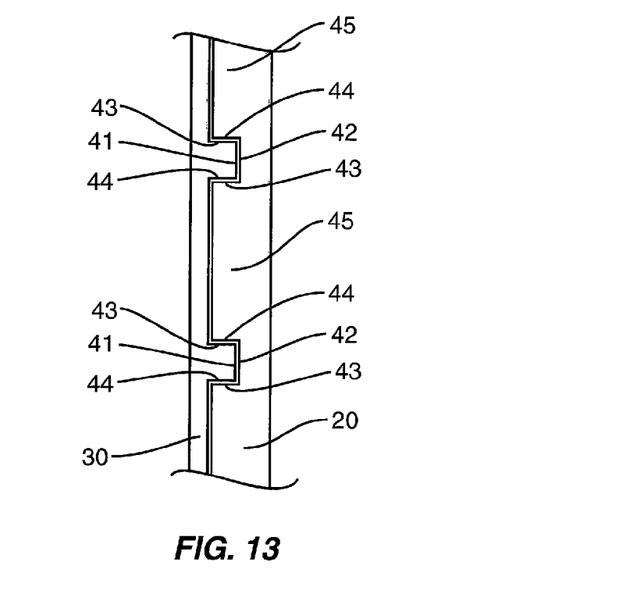
FIG. 13 is a partial schematic view of helical supports according to one embodiment.

The shapes and orientations of the superior and inferior sides 43, 44 may vary. In one embodiment as illustrated in FIGS. 12A-12C, inferior edges 44 of the teeth 45 and superior edges 43 of the splines include a shallow angle. In another embodiment as illustrated in FIG. 13, each side 43, 44 extends outward from the respective body 21, 31 at a substantially perpendicularly angle. This configuration may provide a more secure engagement between the supports 40, but may require more axial force to adjust the height.

The implants 10 may be inserted into the spine from a variety of approaches. One embodiment includes accessing the spine from an anterior approach. Other applications contemplate other approaches, including posterior, postero-lateral, antero-lateral and lateral approaches to the spine. Further, the implants 10 may be used with the various regions of the spine, including the cervical, thoracic, lumbar and/or sacral regions.

In one embodiment as illustrated in FIG. 1, the outer member 30 extends completely around the inner member 20. In another embodiment, the outer member 30 may extend around a section of the inner member 20. A slot 33 may extend the length of the outer member 30 from a top edge to a bottom edge thereby forming an open section.

Spatially relative terms such as "under", "below", "over", "inferior", "superior", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc and are also not intended to be limiting. Like terms refer to like elements throughout the description.

As used herein, the terms "having", "containing", "including", "comprising" and the like are open ended terms that indicate the presence of stated elements or features, but do not preclude additional elements or features. The articles "a", "an" and "the" are intended to include the plural as well as the singular, unless the context clearly indicates otherwise.

The present invention may be carried out in other specific ways than those herein set forth without departing from the scope and essential characteristics of the invention. In the embodiments described above, the inner member 20 and the outer member 30 are substantially straight. Members 20, 30 may also be curved. The present embodiments are, therefore, to be considered in all respects as illustrative and not restrictive, and all changes coming within the meaning and equivalency range of the appended claims are intended to be embraced therein.

What is claimed is:

1. An implant for spacing apart vertebral members comprising:

an outer member comprising a first helical support that extends along an inner side of the outer member; and an inner member arranged in a telescoping manner with the outer member, the inner member comprising a second helical support that extends along an outer side of the inner member;

the first and second helical supports wrapping around their respective members in different directions to bind together to prevent rotation;

the inner and outer members being axially movable in an outward direction to increase a height of the implant with the first and second helical supports engaging together to maintain the height.

2. The implant of claim 1, wherein the inner and outer members include a common cross-sectional shape.

3. The implant of claim 2, wherein the inner and outer members are polygonal.

4. The implant of claim 1, wherein the outer member further comprises at least one longitudinal slot to radially increase an interior region to allow the axial movement between the inner and outer members.

5. The implant of claim 4, wherein the outer member further comprises a non-slotted section, the first helical support being positioned away from the non-slotted section.

6. The implant of claim 1, wherein the first and second helical supports each include a superior side and an inferior side, with the sides extending from the inner and outer members at angles requiring a first force to axially move the members in the outward direction, and requiring a second, greater force to axially move the members in an inward direction.

7. The implant of claim 1, wherein at least one of the helical supports comprises a plurality of teeth that are separated by one or more cuts, the plurality of teeth extend radially outward beyond a floor of the cuts.

8. The implant of claim 1, wherein the outer member is constructed of at least two separate sections that are connected together.

9. The implant of claim 1, further comprising an extension that fits within a slot and prevent rotation between the inner and outer members.

10. An implant for spacing apart vertebral members comprising:

inner and outer members arranged in a telescoping manner; and helical supports extending along the inner and outer members and being shaped to prevent relative rotation between the inner and outer members;

the inner and outer members being axially movable in an outward direction to increase a height of the implant with the helical supports of the inner and outer members engaging together to maintain the height.

11. The implant of claim 10, wherein the helical supports include a superior side and an inferior side with the superior and inferior sides being oriented to require a first force to axial move the inner and outer members in the outward direction to increase the height, and a second, greater force to move the inner and outer members in an inward direction to lessen the height.

12. The implant of claim 10, wherein the inner and outer members each include a polygonal shape.

13. The implant of claim 10, further comprising at least one slot within the outer member for the outer member to radially expand during the axial movement.

14. An implant for spacing apart vertebral members comprising:

an inner member comprising first and second helical supports each extending outward from an outer surface with a first helical cut extending in a first direction and a second helical cut extending in a second direction; and an outer member including a hollow interior sized to receive the inner member, the outer member including a inner surface with third and fourth helical supports extending outward from the inner surface and sized to engage with the first and second helical supports.

15. The implant of claim 14, wherein the inner and outer members include a common cross-sectional shape.

16. The implant of claim 14, wherein the inner and outer members include a polygonal cross-sectional shape with at least one slot positioned within a corner of the outer member.

17. The implant of claim 14, wherein at least one of the helical supports comprises teeth that are substantially rectangular with a pair of the superior sides and a pair of the inferior sides.

18. The implant of claim 14, further comprising at least one slot that extends axially along the outer member a distance from a first edge inward to a second point located along a length of the outer member, with the first and second helical supports each including a length less than or equal to the distance and being positioned between the first edge and the second point.

19. An implant for spacing apart vertebral members comprising:

a first member comprising a first helical support that extend over a length of the first member, the first member further comprising a slot;

a second member comprising a second helical support and an extension;

the first and second members in a telescoping arrangement with the helical supports engaging and disengaging during axial movement and the extension is sized to fit within the slot to prevent relative rotation between the first and second members.

20. The implant of claim 19, wherein the slot is substantially straight.

* * * * *